(12) United States Patent
Whitehurst et al.

(10) Patent No.: US 7,167,751 B1
(45) Date of Patent: Jan. 23, 2007

(54) METHOD OF USING A FULLY IMPLANTABLE MINIATURE NEUROSTIMULATOR FOR VAGUS NERVE STIMULATION

(75) Inventors: Todd K Whitehurst, Santa Clarita, CA (US); James P McGivern, Stevenson Ranch, CA (US)

(73) Assignee: Advanced Bionics Corporation, Valencia, CA (US)

(*) Notice: Subject to any disclaimer, the term of this patent is extended or adjusted under 35 U.S.C. 154(b) by 0 days.

(21) Appl. No.: 10/993,989

(22) Filed: Nov. 19, 2004

Related U.S. Application Data

(62) Division of application No. 10/081,820, filed on Feb. 19, 2002.

(60) Provisional application No. 60/272,531, filed on Mar. 1, 2001.

(51) Int. Cl.
 *A61N 1/08* (2006.01)
(52) U.S. Cl. ...................................... 607/40
(58) Field of Classification Search .................. 607/1, 607/46, 116, 45, 118, 40, 41
 See application file for complete search history.

(56) References Cited

U.S. PATENT DOCUMENTS

| | | | |
|---|---|---|---|
| 4,702,254 A | 10/1987 | Zabara | |
| 4,867,164 A | 9/1989 | Zabara | |
| 5,188,104 A | 2/1993 | Wernicke et al. | |
| 5,193,539 A | 3/1993 | Schulman et al. | |
| 5,193,540 A | 3/1993 | Schulman et al. | |
| 5,215,086 A | 6/1993 | Terry, Jr. et al. | |
| 5,222,494 A | 6/1993 | Baker, Jr. | |
| 5,231,988 A | 8/1993 | Wernicke et al. | |
| 5,269,303 A | 12/1993 | Wernicke et al. | |
| 5,299,569 A | 4/1994 | Wernicke et al. | |
| 5,312,439 A | 5/1994 | Loeb | |
| 5,330,507 A | 7/1994 | Schwartz | |
| 5,330,515 A | 7/1994 | Rutecki et al. | |
| 5,335,657 A | 8/1994 | Terry, Jr. et al. | |
| 5,522,862 A | 6/1996 | Testerman et al. | |
| 5,540,730 A | 7/1996 | Terry, Jr. et al. | |
| 5,571,150 A | 11/1996 | Wernicke et al. | |
| 5,700,282 A | 12/1997 | Zabara | |
| 5,707,400 A | 1/1998 | Terry, Jr. et al. | |

(Continued)

FOREIGN PATENT DOCUMENTS

WO    WO-93/01862 A1    2/1993

(Continued)

OTHER PUBLICATIONS

Bilgutay, et al., "Vagal Tuning: A New concept in the Treatment of Supraventricular Arrhythmias, Angina Pectoris, and Heart Failure", Journal of Thoracic and Cardiovascular Surgery, vol. 56, No. 1, (Jul. 1968), pp. 71-82.

(Continued)

*Primary Examiner*—Mark Bockelman
(74) *Attorney, Agent, or Firm*—Laura Haburay Bishop; Travis K. Laird

(57) ABSTRACT

A method of using a small implantable stimulator(s) with at least two electrodes small enough to have the electrodes located adjacent to the vagus nerve. The small stimulator provides a means of stimulating the vagus nerve when desired, and may be implanted via a minimal surgical procedure.

19 Claims, 7 Drawing Sheets

U.S. PATENT DOCUMENTS

| | | | |
|---|---|---|---|
| 5,928,272 | A | 7/1999 | Adkins et al. |
| 6,051,017 | A | 4/2000 | Loeb et al. |
| 6,104,956 | A | 8/2000 | Naritoku et al. |
| 6,185,452 | B1 | 2/2001 | Schulman et al. |
| 6,205,359 | B1 | 3/2001 | Boveja |
| 6,208,902 | B1 | 3/2001 | Boveja |
| 6,269,270 | B1 | 7/2001 | Boveja |
| 6,341,236 | B1 | 1/2002 | Osorio et al. |
| 6,356,788 | B1 | 3/2002 | Boveja |
| 6,366,814 | B1 | 4/2002 | Boveja et al. |
| 6,464,687 | B1 | 10/2002 | Ishikawa et al. |
| 6,473,644 | B1 | 10/2002 | Terry, Jr. et al. |
| 6,479,523 | B1 | 11/2002 | Puskas |
| 6,721,603 | B1 | 4/2004 | Zabara et al. |
| 6,760,626 | B1 | 7/2004 | Boveja |
| 6,788,975 | B1 | 9/2004 | Whitehurst et al. |
| 2002/0087192 | A1 | 7/2002 | Barrett et al. |

FOREIGN PATENT DOCUMENTS

| | | |
|---|---|---|
| WO | WO-93/02744 A1 | 2/1993 |
| WO | WO-94/00185 A1 | 1/1994 |
| WO | WO-94/00188 A1 | 1/1994 |
| WO | WO-94/00189 A1 | 1/1994 |
| WO | WO-98/37926 A1 | 9/1998 |
| WO | WO-98/43700 A1 | 10/1998 |
| WO | WO-98/43701 A1 | 10/1998 |
| WO | WO-01-00273 A1 | 1/2001 |
| WO | WO-02/04068 A1 | 1/2002 |

OTHER PUBLICATIONS

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

Handforth, et al., "Suppression of Harmaline-Induced Tremor in Rats by Vagus Nerve Stimulation", Movement Disorders, vol. 16(1), (Jan. 2001), pp. 84-88.

Handforth, et al., "Effect of Vagus Nerve Stimulation on Essential Tremor", Neurology, vol. 54 Suppl. 3, (2000), pp. A238.

Rush, et al., "Vagus Nerve Stimulation (VNS) for Treatment-Resistant Depressions: A Multicenter Study", Society of Biological Psychiatry, vol. 47, (2000), pp. 276-286.

Walker, et al., "Regulation of Limbic Motor Seizures by GABA and Glutamate Transmission in Nucleus Tractus Solitarius", Epilepsia, vol. 40(8), (Aug. 1999), pp. 1051-1057.

Whitehurst inventor for AB-223U; U.S. Appl. No. 10/428,743, filed May 2, 2003; entitled "Treatment of Epilepsy by Brain Stimulation".

Whitehurst, et al. Inventors for AB-166U; U.S. Appl. No. 10/176,722, filed Jun. 20, 2002; entitled "Vagus Nerve Stimulation via Unidirectional Propagation of Action Potentials".

Whitehurst, et al. Inventors for AB-272U; U.S. Appl. No. 10/178,010, filed Jun. 20, 2002; entitled "Implantable Microstimulators for Unidirectional Propagation of Action Potentials".

Whitehurst, et al. Inventors for AB-276U; U.S. Appl. No. 10/810,091, filed Mar. 26, 2004; entitled "Treatment of Movement Disorders with Drug Therapy".

METHOD OF USING A FULLY IMPLANTABLE MINIATURE NEUROSTIMULATOR FOR VAGUS NERVE STIMULATION

The present application is a Divisional of U.S. application Ser. No. 10/081,820, filed Feb. 19, 2002; which claims the benefit of U.S. Provisional Application Ser. No. 60/272,531, filed Mar. 1, 2001, which applications are incorporated herein by reference.

FIELD OF THE INVENTION

The present invention generally relates to implantable stimulator systems, and more particularly relates to an implantable stimulator system utilizing one or more implantable microstimulators for vagus nerve stimulation.

BACKGROUND OF THE INVENTION

Epilepsy is characterized by a tendency to recurrent seizures that can lead to loss of awareness, loss of consciousness, and/or disturbances of movement, autonomic function, sensation (including vision, hearing and taste), mood, and/or mental function. Epilepsy afflicts 1–2% of the population in the developed world. The mean prevalence of active epilepsy (i.e., continuing seizures or the need for treatment) in developed and undeveloped countries combined is estimated to be 7 per 1,000 of the general population, or approximately 40 million people worldwide. Studies in developed countries suggest an annual incidence of epilepsy of approximately 50 per 100,000 of the general population. However, studies in developing countries suggest this figure is nearly double at 100 per 100,000.

Epilepsy is often but not always the result of underlying brain disease. Any type of brain disease can cause epilepsy, but not all patients with the same brain pathology will develop epilepsy. The cause of epilepsy cannot be determined in a number of patients; however, the most commonly accepted theory posits that it is the result of an imbalance of certain chemicals in the brain, e.g., neurotransmitters. Children and adolescents are more likely to have epilepsy of unknown or genetic origin. The older the patient, the more likely it is that the cause is an underlying brain disease such as a brain tumor or cerebrovascular disease.

Trauma and brain infection can cause epilepsy at any age, and in particular, account for the higher incidence rate in developing countries. For example, in Latin America, neurocysticercosis (cysts on the brain caused by tapeworm infection) is a common cause of epilepsy; in Africa, AIDS and its related infections, malaria and meningitis, are common causes; in India, AIDS, neurocysticercosis and tuberculosis, are common causes. Febrile illness of any kind, whether or not it involves the brain, can trigger seizures in vulnerable young children, which seizures are called febrile convulsions. About 5% of such children go on to develop epilepsy later in life. Furthermore, for any brain disease, only a proportion of sufferers will experience seizures as a symptom of that disease. It is, therefore, suspected that those who do experience such symptomatic seizures are more vulnerable for similar biochemical/neurotransmitter reasons.

Movement disorders are neurologic syndromes characterized by either an excess or a paucity of movement. These disorders affect approximately two million Americans, including over one million suffering from benign essential tremor, and half a million suffering from Parkinson's disease. A substantial percentage of those afflicted with movement disorders experience a significant decrease in quality of life, suffering such problems as incapacitating tremor, limited mobility, bradykinesia (difficulty consciously initiating movement), dysarthria (difficulty with speech), and consequent social isolation. The etiology of many movement disorders, e.g., benign essential tremor, is poorly understood. For other movement disorders, e.g., Parkinson's disease, the mechanism of the disorder and even the brain cells affected have been identified, but even with optimal medication and physician care the disease may not be reversed and may even continue to progress. Medications that are effective for movement disorders may have significant side effects and may lose their efficacy over time.

Essential Tremor (ET), a.k.a., Benign Essential Tremor, is the most common movement disorder. It is a syndrome characterized by a slowly progressive postural and/or kinetic tremor, usually affecting both upper extremities. The prevalence of ET in the US is estimated at 0.3–5.6% of the general population. A 45-year study of ET in Rochester, Minn. reported an age- and gender-adjusted prevalence (i.e., the percentage of a population that is affected with a particular disease at a given time) of 305.6 per 100,000 and an incidence (i.e., the rate of new cases of a particular disease in a population being studied) of 23.7 per 100,000.

ET affects both sexes equally. The prevalence of ET increases with age. There are bimodal peaks of onset—one in late adolescence to early adulthood and a second peak in older adulthood. The mean age at presentation is 35–45 years. ET usually presents by 65 years of age and virtually always by 70 years. Tremor amplitude slowly increases over time. Tremor frequency decreases with increasing age. An 8–12 Hz tremor is seen in young adults and a 6–8 Hz tremor is seen in the elderly. Although ET is progressive, no association has been found between age of onset and severity of disability.

Mortality rates are not increased in ET. However, disability from ET is common. Significant changes in livelihood and socializing are reported by 85% of individuals with ET, and 15% report being seriously disabled due to ET. Decreased quality of life results from both loss of function and embarrassment. In a study of hereditary ET, 60% did not seek employment; 25% changed jobs or took early retirement; 65% did not dine out; 30% did not attend parties, shop alone, partake of a favorite hobby or sport, or use public transportation; and 20% stopped driving.

BRIEF SUMMARY OF THE INVENTION

The invention disclosed and claimed herein provides means for chronically stimulating the vagus nerve with a miniature implantable neurostimulator that can be implanted with a minimal surgical procedure. Electrical stimulation of the vagus nerve may provide significant therapeutic benefit in the treatment, control, and/or prevention of epilepsy, metabolic disorders (including obesity), mood disorders (including depression and bipolar disorder), anxiety disorders (including generalized anxiety disorder and obsessive-compulsive disorder), chronic pain (including visceral pain, neuropathic pain and nociceptive pain), gastrointestinal disorders (including gastroesophageal reflux disease (GERD), fecal dysfunction, gastrointestinal ulcer, gastroparesis, and other gastrointestinal motility disorders), hypertension, cardiac disorders (including tachycardia, bradycardia, other arrhythmias, congestive heart failure, and angina pectoris), psychotic disorders (including schizophrenia), cognitive disorders, dementia (including Alzheimer's disease, Pick's disease, and multi-infarct dementia), eating disorders (including anorexia nervosa and bulimia), sleep disorders (including insomnia, hypersomnia, narcolepsy, and sleep apnea), endocrine disorders (including diabetes), movement disorders (including Parkinson's disease and essential tremor), and/or headache (including migraine and chronic daily headache). To stimulate the vagus nerve, a miniature implantable neurostimulator, such as a Bionic Neuron (also referred to as a BION™ microstimulator) may be implanted via a minimal surgical procedure (e.g., small incision and/or via endoscopic placement) adjacent to one or more portions of the vagus nerve (including vagus nerve branches).

A microstimulator may be implanted via a small incision and/or via endoscopic means. A more complicated surgical procedure may be required for sufficient access to the nerve or portion of the nerve (e.g., nerve fibers surrounded by scar tissue) or for purposes of fixing the neurostimulator in place. A single microstimulator may be implanted, or two or more microstimulators may be implanted to achieve greater stimulation of the nerve fibers.

The microstimulator used with the present disclosure possesses one or more of the following properties, among others:

- at least two electrodes for applying stimulating current to surrounding tissue;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the microstimulator; and
- a form factor making the microstimulator implantable via a minimal surgical procedure.

A microstimulator may operate independently, or in a coordinated manner with other implanted devices, or with external devices. For instance, a microstimulator may incorporate means for sensing a patient's condition, which it may then use to control stimulation parameters in a closed loop manner. The sensing and stimulating means may be incorporated into a single microstimulator, or a sensing means may communicate sensed information to at least one microstimulator with stimulating means.

BRIEF DESCRIPTION OF THE SEVERAL VIEWS OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

Figure 1A:
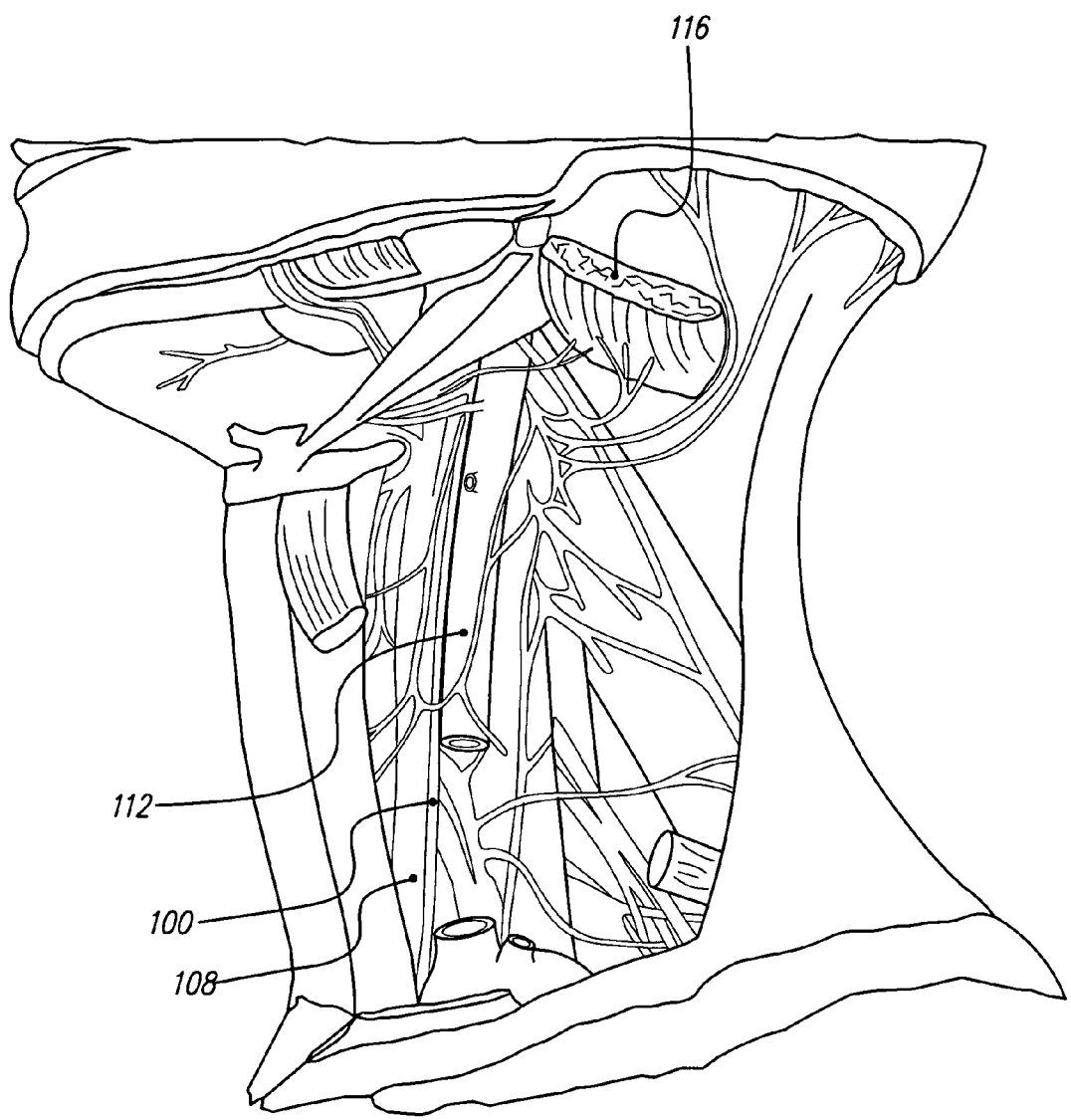
FIG. 1A depicts various nerves, muscles, arteries, and veins in the neck.

The following description is of the best mode presently contemplated for carrying out the invention. This description is not to be taken in a limiting sense, but is made merely for the purpose of describing the general principles of the invention. The scope of the invention should be determined with reference to the claims.

Recent studies in both developed and developing countries have shown that up to 70% of newly diagnosed children and adults with epilepsy can be successfully treated (i.e., complete control of seizures for several years) with anti-epileptic drugs. After two to five years of successful treatment, drugs can be withdrawn in about 70% of children and 60% of adults without the patient experiencing relapses. However, up to 30% of patients are refractory to medication. There is evidence that the longer the history of epilepsy, the harder it is to control. The presence of an underlying brain disease typically results in a worse prognosis in terms of seizure control. Additionally, partial seizures, especially if associated with brain disease, are more difficult to control than generalized seizures.

Vagus nerve stimulation is currently used as a therapy for refractory epilepsy, and studies have suggested that such stimulation may also be an efficacious therapy for tremor, depression, obesity, and gastroesophageal reflux disease (GERD). The only currently available vagus nerve stimulator requires a significant surgical procedure for placement. Additionally, the pulse generator is battery-powered, which battery needs to be changed periodically, and the pulse generator may be uncomfortable and cosmetically unpleasing as well.

In 2001, Handforth, et al. studied whether vagus nerve stimulation could suppress tremor in the harmaline tremor model in the rat. [See Handforth, et al., "Suppression of harmaline-induced tremor in rats by vagus nerve stimulation" *Movement Disorders* 2001. January; 16(1):84–8.] Animals were chronically implanted with helical leads around the left vagus nerve and a disk-shaped electrode was positioned subcutaneously in the dorsal neck. Harmaline-induced tremor was recorded on a physiograph while each animal received a sequence of five 20-minute trials. Each trial consisted of five minutes of pre-stimulation baseline, five minutes of vagus nerve stimulation, and ten minutes of post-stimulation. Vagus nerve stimulation significantly suppressed harmaline-induced tremor. The suppressive effect was present within the first minute of stimulation and was reproducible across the five trials of the study. The results of this study suggest that the central generator or expression of tremor in the harmaline animal model can be suppressed by vagus nerve stimulation. This further suggest that vagus nerve stimulation may be an effective therapy for essential tremor and perhaps for other movement disorders.

Patients suffering from tremor and other symptoms may undergo surgery to lesion a part of the brain, which may afford some relief. However, a lesion is irreversible, and it may lead to side effects such as dysarthria or cognitive disturbances. Additionally, lesions generally yield effects on only one side (the contralateral side), and bilateral lesions are significantly more likely to produce side effects. Other surgical procedures, such as fetal tissue transplants, are costly and unproven.

Patients suffering from epilepsy may undergo surgery to remove a part of the brain in which the seizures are believed to arise, i.e., the seizure focus. However, in many patients a seizure focus cannot be identified, and in others the focus is in an area that cannot be removed without significant detrimental impact on the patient. For example, in temporal lobe epilepsy, patients may have a seizure focus in the hippocampi bilaterally. However, both hippocampi cannot be removed without devastating impacts on long-term memory. Other patients may have a seizure focus that lies adjacent to a critical area such as the speech center.

Vagus nerve stimulation (VNS) has been applied with some success in patients with refractory epilepsy. In the existing procedure, an implantable pulse generator (IPG) is implanted in the patient's thorax, and an electrode lead is routed from the IPG to the left vagus nerve in the neck. Helix-shaped stimulation and indifferent electrodes are attached to the vagus nerve via an invasive surgical process that requires the carotid sheath to be fully exposed. Based on a number of studies, approximately 5% of patients undergoing VNS are seizure-free, and an additional 30–40% of patients have a greater than 50% reduction in seizure frequency.

Drawbacks of available VNS, such as size (of internal and/or external components), discomfort, inconvenience, and/or complex, risky, and expensive surgical procedures, has generally confined their use to patients with severe symptoms and the capacity to finance the surgery. Recently, an alternative to bulky implantable stimulation assemblies has been introduced. Small, implantable microstimulators can be implanted via a small incision into soft tissues through a cannula or needle. See, e.g., U.S. Pat. Nos. 5,324,316 and 5,405,367, both of which patents are incorporated herein by reference. Discussed herein are ways to effectively use such small, fully implantable, chronic neurostimulators for vagus nerve stimulation.

Figure 1B:
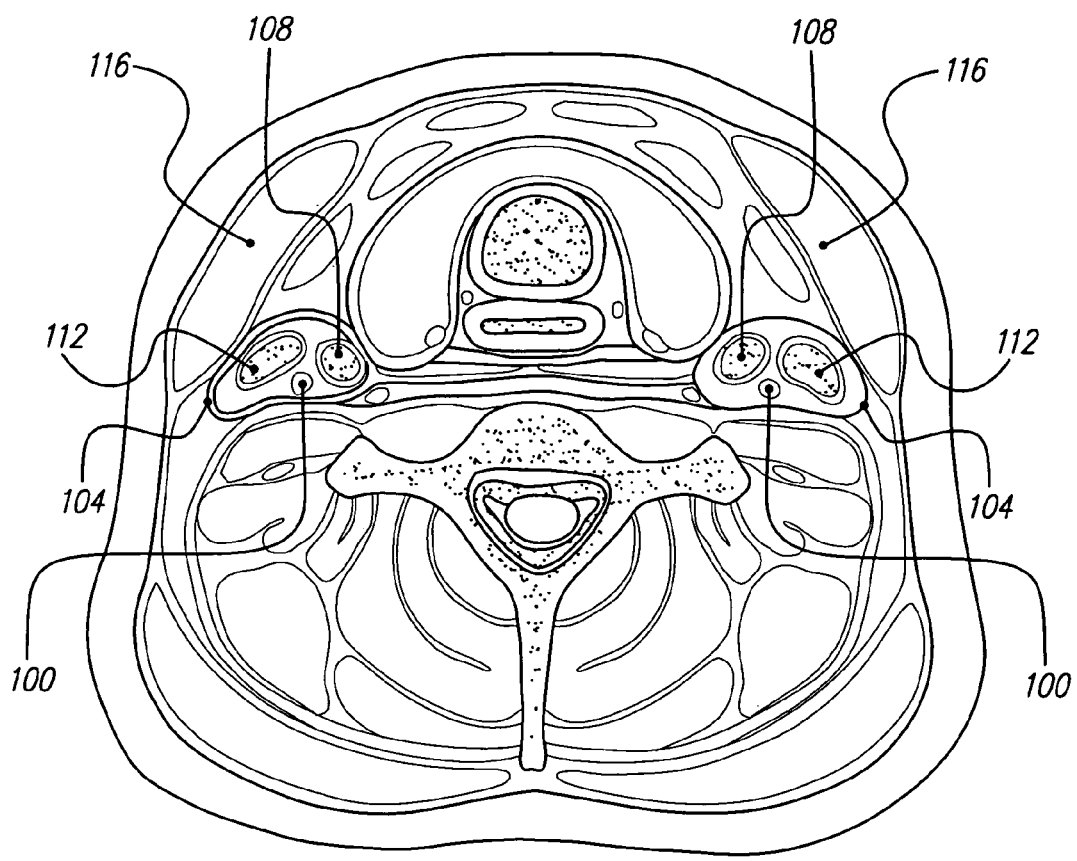
FIG. 1B is a cross-section through the neck, at the level of cervical vertebra C7.

FIG. 1A depicts nerves, muscles, arteries, and veins in the neck, while FIG. 1B is a cross-section through the neck, at the level of cervical vertebra C7. As can be seen, the vagus nerve 100 is relatively easily accessible in the neck. The vagus nerve lies within the carotid sheath 104, along with the common carotid artery 108 and the internal jugular vein 112. The carotid sheath 104 lies beneath the sternocleidomastoid muscle 116, which, in FIG. 1A, is cut and turned up.

Figure 2A:
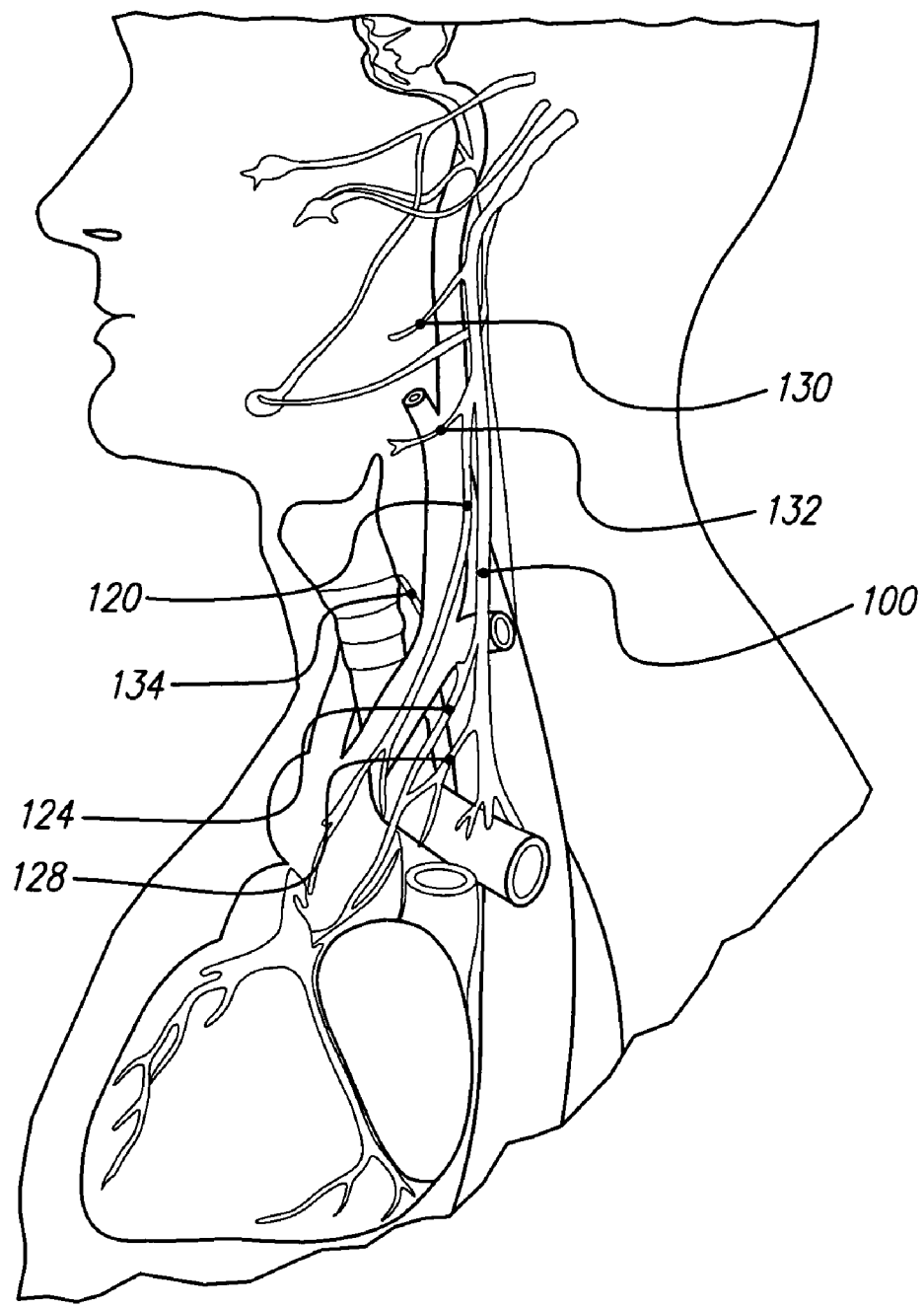
FIGS. 2A and 2B illustrate various autonomic nerves in the head, neck, thorax, and abdomen.
Figure 2B:
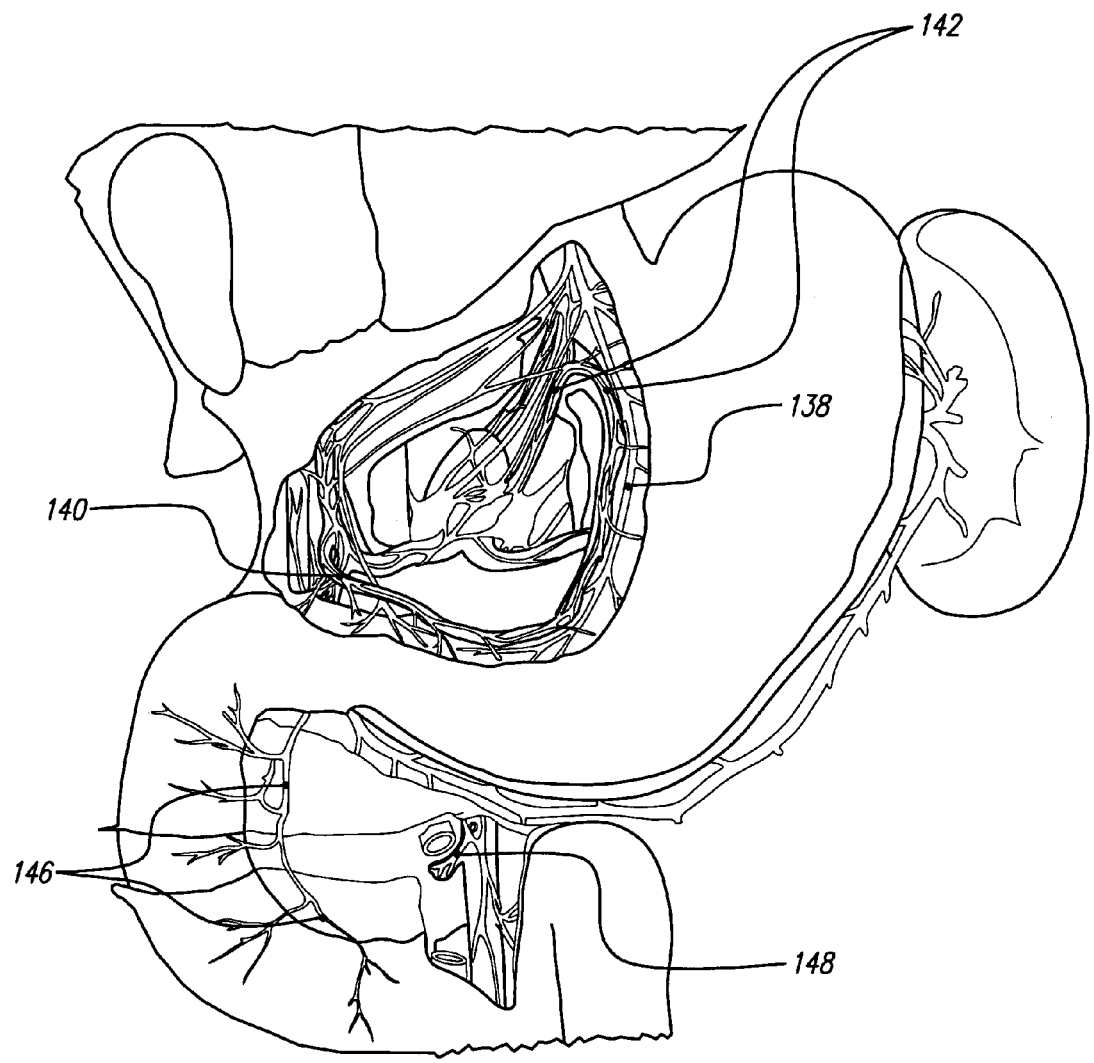

FIGS. 2A and 2B illustrate various autonomic nerves in the head, neck, thorax, and abdomen. The vagus nerve 100 has a number of nerve branches. Three of these branches are named the superior cervical cardiac branch 120, the inferior cervical cardiac branch 124, and the thoracic cardiac branch 128. Advantageously, these branches are sufficiently separate from the vagus nerve 100 to allow independent and selective stimulation of the vagus nerve 100 and/or its branches via appropriate placement of a microstimulator(s).

In accordance with the teachings of the present disclosure and as discussed in more detail presently, electrical stimulation at one or more locations along the vagus nerve 100 and/or its branches is provided to treat, control, and/or prevent epilepsy, metabolic disorders (including obesity), mood disorders (including depression and bipolar disorder), anxiety disorders (including generalized anxiety disorder and obsessive-compulsive disorder), chronic pain (including visceral pain, neuropathic pain and nociceptive pain), gastrointestinal disorders (including gastroesophageal reflux disease (GERD), fecal dysfunction, gastrointestinal ulcer, gastroparesis, and other gastrointestinal motility disorders), hypertension, cardiac disorders (including tachycardia, bradycardia, other arrhythmias, congestive heart failure, and angina pectoris), psychotic disorders (including schizophrenia), cognitive disorders, dementia (including Alzheimer's disease, Pick's disease, and multi-infarct dementia), eating disorders (including anorexia nervosa and bulimia), sleep disorders (including insomnia, hypersomnia, narcolepsy, and sleep apnea), endocrine disorders (including diabetes), movement disorders (including Parkinson's disease and essential tremor), and/or headache (including migraine and chronic daily headache). A microstimulator may be relatively easily implanted adjacent the vagus nerve via a small incision and/or via endoscopic means.

Stimulation of the vagus nerve may occur distal to (i.e., below) the superior cervical cardiac branch 120, or distal to both the superior cervical cardiac branch 120 and the inferior cervical cardiac branch 124, and may, for instance, be applied to the left vagus nerve. Stimulation of the left vagus nerve distal to the superior cervical cardiac branch 120 and/or the inferior cervical cardiac branch 124 does not pose the cardiac risks that can be associated with vagus nerve stimulation applied proximal to one or both of these nerve branches. Alternatively, some patients may benefit from vagus nerve stimulation applied distal to the thoracic cardiac branch 128.

As used herein, stimulation of the vagus nerve may include stimulation of the vagus nerve and/or one or more of its branches. For instance, to relieve sleep disorders (such as insomnia, hypersomnia, narcolepsy, sleep apnea, and the like), the vagus nerve may be stimulated. More specifically, one or more of the pharyngeal branch of the vagus nerve 130, the superior laryngeal branch of the vagus nerve 132, the pharyngeal plexus (not shown), the left and/or right recurrent laryngeal branch of the vagus nerve 134, and/or other branches of the vagus nerve may be stimulated to relieve sleep disorders. As another example, the vagus nerve may be stimulated to relieve gastrointestinal disorders (such as including gastroesophageal reflux disease (GERD), fecal dysfunction, gastrointestinal ulcer, gastroparesis, and other gastrointestinal motility disorders). More specifically, one or more of the gastrointestinal branches of the vagus nerve, such as the anterior gastric branch of the anterior vagal trunk 138, the right gastric plexus 140, and/or the left gastric plexus 142 may be stimulated to relieve gastrointestinal disorders. As yet another example, to relieve endocrine disorders (including diabetes), the vagus nerve may be stimulated. More specifically, one or more branches innervating the pancreas, such as the anterior superior and anterior inferior pancreaticoduodenal plexus 146, the posterior pancreaticoduodenal plexus (not shown), the inferior pancreaticoduodenal plexus 148, or the like may be stimulated to relieve endocrine disorders.

The present disclosure is directed to treating the aforementioned types of conditions using one or more small, implantable neurostimulators, referred to herein as "microstimulators". The microstimulators of the present disclosure are preferably similar to or of the type referred to as BION™ devices. The following documents describe various features and details associated with the manufacture, operation, and use of BION implantable microstimulators, and are all incorporated herein by reference:

| Application/Patent/ Publication No. | Filing/Publication Date | Title |
|---|---|---|
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 5,324,316 | Issued Jun. 28, 1994 | Implantable Microstimulator |
| U.S. Pat. No. 5,405,367 | Issued Apr. 11, 1995 | Structure and Method of Manufacture of an Implantable Microstimulator |
| U.S. Pat. No. 6,051,017 | Issued Apr. 18, 2000 | Improved Implantable Microstimulator and Systems Employing Same |
| PCT Publication WO 98/37926 | published Sep. 3, 1998 | Battery-Powered Patient Implantable Device |
| PCT Publication WO 98/43700 | published Oct. 8, 1998 | System of Implantable Devices For Monitoring and/or Affecting Body Parameters |
| PCT Publication WO 98/43701 | published Oct. 8, 1998 | System of Implantable Devices For Monitoring and/or Affecting Body Parameters |
| | published September 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

Figure 3:
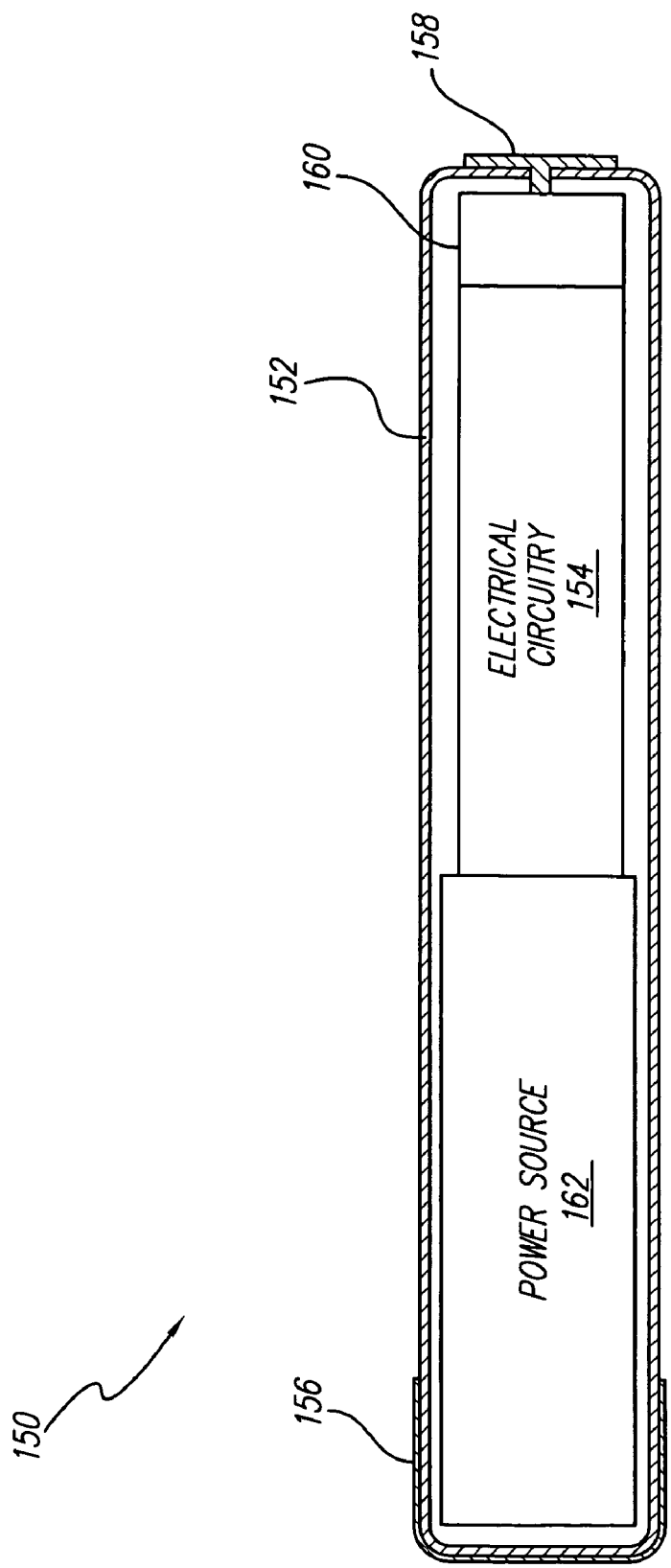
FIG. 3 illustrates an exemplary embodiment of a system of the present disclosure.

As shown in FIG. 3, microstimulator device 150 includes a narrow, elongated capsule 152 containing electronic circuitry 154 connected to electrodes 156 and 158, which may pass through the walls of the capsule at either end. As detailed in the referenced patent publications, electrodes 156 and 158 generally comprise a stimulating electrode (to be placed close to the nerve) and an indifferent electrode (for completing the circuit). Other configurations of microstimulator device 150 are possible, as is evident from the above-referenced publications, and as described in more detail herein.

Certain configurations of implantable microstimulator 150 are sufficiently small to permit its placement adjacent to the structures to be stimulated. (As used herein, "adjacent" and "near" mean as close as reasonably possible to the target nerve, including touching or even being positioned within the target nerve, but in general, may be as far as about 150 mm from the target nerve.) A single microstimulator 150 may be implanted, or two or more microstimulators may be implanted to achieve greater stimulation of the nerve fibers, or for a longer period of time.

Capsule 152 of FIG. 3 may have a diameter of about 4–5 mm, or only about 3 mm, or even less than about 3 mm. Capsule 152 length may be about 25–35 mm, or only about 20–25 mm, or even less than about 20 mm. The shape of the microstimulator may be determined by the structure of the desired target, the surrounding area, and the method of implantation. A thin, elongated cylinder with electrodes at the ends, as shown in FIG. 3, is one possible configuration, but other shapes, such as spheres, disks, or helical structures, are possible, as are additional electrodes.

Microstimulator 150 may be implanted with a surgical insertion tool specially designed for the purpose, or may be placed, for instance, via a small incision and through an insertion cannula. Alternatively, device 150 may be implanted via conventional surgical methods, or may be inserted using other endoscopic or laparoscopic techniques. A more complicated surgical procedure may be required for sufficient access to a nerve or a portion of a nerve (e.g., nerve fibers surrounded by scar tissue, or more distal portions of the nerve) and/or for fixing the neurostimulator in place.

The external surfaces of stimulator 150 may advantageously be composed of biocompatible materials. Capsule 152 may be made of, for instance, glass, ceramic, or other material that provides a hermetic package that will exclude water vapor but permit passage of electromagnetic fields used to transmit data and/or power. Electrodes 156 and 158 may be made of a noble or refractory metal or compound, such as platinum, iridium, tantalum, titanium, titanium nitride, niobium, or alloys of any of these, in order to avoid corrosion or electrolysis which could damage the surrounding tissues and the device.

In certain embodiments of the present disclosure, microstimulator 150 comprises two, leadless electrodes. However, either or both electrodes 156 and 158 may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to a specific nerve structure(s) a short distance from the surgical fixation of the bulk of the implantable stimulator 150, while allowing most elements of stimulator 150 to be located in a more surgically convenient site. This minimizes the distance traversed and the surgical planes crossed by the device and any lead(s). In most uses of this disclosure, the leads are no longer than about 150 mm.

Microstimulator 150 contains, when necessary and/or desired, electronic circuitry 154 for receiving data and/or power from outside the body by inductive, radio-frequency (RF), or other electromagnetic coupling. In some embodiments, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

Neurostimulator 150 includes, when necessary and/or desired, a programmable memory 160 for storing a set(s) of data, stimulation, and control parameters. Among other things, memory 160 may allow stimulation and control parameters to be adjusted to settings that are safe and efficacious with minimal discomfort for each individual. Specific parameters may provide therapeutic advantages for various medical conditions, their forms, and/or severity. For instance, some patients may respond favorably to intermittent stimulation, while others may require continuous stimulation to alleviate their symptoms.

In addition, stimulation parameters may be chosen to target specific neural populations and to exclude others, or to increase neural activity in specific neural populations and to decrease neural activity in others. For example, relatively low frequency neurostimulation (i.e., less than about 50–100 Hz) typically has an excitatory effect on surrounding neural tissue, leading to increased neural activity, whereas relatively high frequency neurostimulation (i.e., greater than about 50–100 Hz) may have an inhibitory effect, leading to decreased neural activity.

Some embodiments of implantable stimulator 150 also includes a power source and/or power storage device 162. Possible power options for a stimulation device of the present disclosure, described in more detail below, include but are not limited to an external power source coupled to stimulator 150, e.g., via an RF link, a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

According to certain embodiments of the present disclosure, a microstimulator operates independently. According to various embodiments of the present disclosure, a microstimulator operates in a coordinated manner with other microstimulator(s), other implanted device(s), or other device(s) external to the patient's body. For instance, a microstimulator may control or operate under the control of another implanted microstimulator(s), other implanted device(s), or other device(s) external to the patient's body. A microstimulator may communicate with other implanted microstimulators, other implanted devices, and/or devices external to a patient's body via, e.g., an RF link, an ultrasonic link, a thermal link, an optical link, or the like. Specifically, a microstimulator may communicate with an external remote control (e.g., patient and/or physician programmer) that is capable of sending commands and/or data to a microstimulator and that may also be capable of receiving commands and/or data from a microstimulator.

Figure 4:
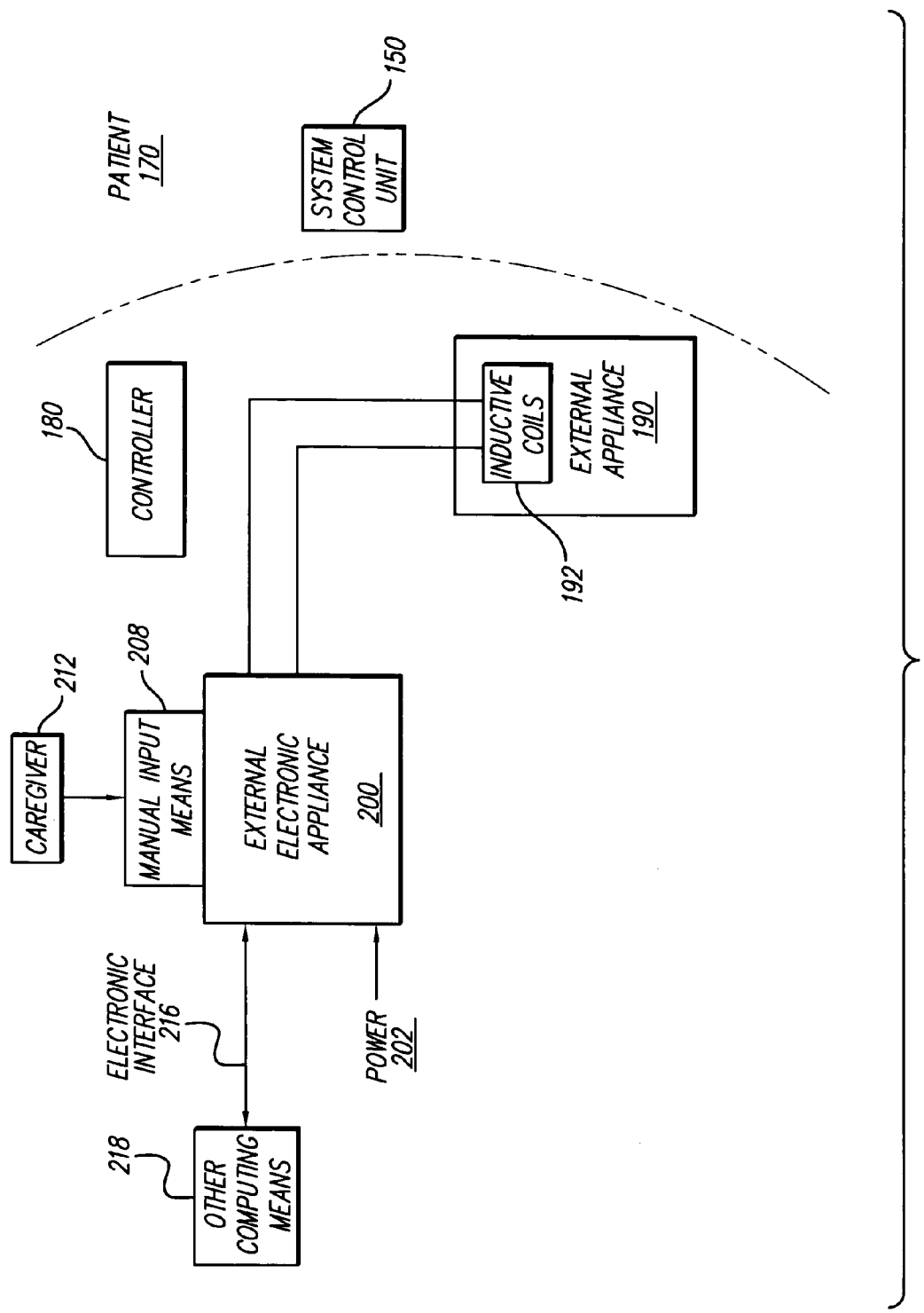
FIG. 4 illustrates preferred external components of the present disclosure.

In certain embodiments, and as illustrated in FIG. 4, the patient 170 switches the implantable stimulator 150 on and off by use of controller 180, which may be handheld. Implantable stimulator 150 is operated by controller 180 by any of various means, including sensing the proximity of a permanent magnet located in controller 180, sensing RF transmissions from controller 180, or the like.

External components for programming and/or providing power to various embodiments of implantable stimulator 150 are also illustrated in FIG. 4. When communication with the implanted stimulator 150 is desired, patient 170 is positioned on or near external appliance 190, which appliance contains one or more inductive coils 192 or other means of communication (e.g., RF transmitter and receiver). External appliance 190 is connected to or is a part of external electronic circuitry appliance 200 which may receive power 202 from a conventional power source. External appliance 200 contains manual input means 208, e.g., a keypad, whereby the patient 170 or a caregiver 212 can request changes in the stimulation parameters produced during the normal operation of the implantable stimulator 150. In these embodiments, manual input means 208 includes various electromechanical switches and/or visual display devices that provide the patient and/or caregiver with information about the status and prior programming of the implantable stimulator 150.

Alternatively or additionally, external electronic appliance 200 is provided with an electronic interface means 216 for interacting with other computing means 218, such as by a serial interface cable or infrared link to a personal computer or to a telephone modem or the like. Such interface means 216 may permit a clinician to monitor the status of the implant and prescribe new stimulation parameters from a remote location.

The external appliance(s) may be embedded in a cushion, pillow, hat, or garment. Other possibilities exist, including a necktie, scarf, patch, or other structure(s) that may be affixed to the patient's body or clothing. External appliances may include a package that can be, e.g., worn on the belt, may include an extension to a transmission coil affixed, e.g., with a velcro band or adhesive, or may be combinations of these or other structures able to perform the functions described herein.

In order to help determine the strength and/or duration of electrical stimulation required to produce the desired effect, in some embodiments, a patient's response to and/or need for treatment is sensed. For example, electrical activity of the brain (e.g., EEG), electrical activity of a nerve (e.g., ENG), muscle activity (e.g., EMG), abnormal movements resulting from a seizure (e.g., accelerometer activity), limb tremor, and/or head tremor may be sensed. Other measures of the state of the patient may additionally or alternatively be sensed. For instance, medication, neurotransmitter, hormone, cytokine, and/or enzyme levels or their changes, and/or levels or changes in other substance(s) borne in the blood and/or in the cerebrospinal fluid (CSF) may be sensed, using, e.g., one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands). For instance, the level or changes in level of neuron-specific enolase, a key glycolytic enzyme, in either or both the blood serum or CSF may be sensed.

For example, when electrodes of implantable stimulator 150 are implanted adjacent to the vagus nerve 100, a sensor or stimulating electrode (or other electrode) of microstimulator 150 may be used to sense changes in EEG resulting from the stimulation applied to the nerve. Alternatively, a "microstimulator" dedicated to sensory processes communicates with a microstimulator that provides the stimulation pulses. The implant circuitry 154 may, if necessary, amplify and transmit these sensed signals, which may be analog or digital. Other methods of determining the required stimulation include a sensor implanted in the brain in an area where altered activity correlates with possible seizures (e.g., the seizure focus and/or near thalamic relay neurons), as well as other methods mentioned herein, and yet others that will be evident to those of skill in the art upon review of the present disclosure. The sensed information may be used to control stimulation parameters in a closed-loop manner.

For instance, in several embodiments of the present disclosure, a first and second "stimulator" are provided. The second "stimulator" periodically (e.g. once per minute) records a level of brain activity (or accelerometer activity, etc.), which it transmits to the first stimulator. The first stimulator uses the sensed information to adjust stimulation parameters according to an algorithm programmed, e.g., by a physician. For example, the amplitude of stimulation may be increased in response to increased activity in brain areas which demonstrate increased activity during epileptic attacks. In some alternatives, one stimulator performs both the sensing and stimulating functions, as discussed in more detail presently.

While a microstimulator may also incorporate means of sensing one or more conditions of the patient, it may alternatively or additionally be desirable to use a separate or specialized implantable device to record and telemeter physiological conditions/responses in order to adjust stimulation parameters. This information may be transmitted to an external device, such as external appliance 190, or may be transmitted directly to implanted stimulator(s) 150. However, in some cases, it may not be necessary or desired to include a sensing function or device, in which case stimulation parameters are determined and refined, for instance, by patient feedback, or the like.

Thus, it is seen that in accordance with the present disclosure, one or more external appliances may be provided to interact with microstimulator 150, and may be used to accomplish, potentially among other things, one or more of the following functions:

Function 1: If necessary, transmit electrical power from the external electronic appliance 200 via appliance 190 to the implantable stimulator 150 in order to power the device and/or recharge the power source/storage device 162. External electronic appliance 200 may include an automatic algorithm that adjusts stimulation parameters automatically whenever the implantable stimulator(s) 150 is/are recharged.

Function 2: Transmit data from the external appliance 200 via the external appliance 190 to the implantable stimulator 150 in order to change the operational parameters (e.g., electrical stimulation parameters) used by stimulator 150.

Function 3: Transmit sensed data indicating a need for treatment or in response to stimulation from neurostimulator 150 (e.g., EEG, change in neurotransmitter or medication level, or other activity) to external appliance 200 via external appliance 190.

Function 4: Transmit data indicating state of the implantable stimulator 150 (e.g., battery level, stimulation settings, etc.) to external appliance 200 via external appliance 190.

By way of example, a treatment modality for epilepsy may be carried out according to the following sequence of procedures:

1. A stimulator 150 is implanted so that its electrodes 156 and 158 are adjacent to the left vagus nerve 100, distal to the inferior cervical cardiac branch 124 of the vagus nerve. If necessary or desired, one or more additional stimulator(s) 150 may additionally or alternatively be implanted adjacent to other areas of the vagus nerve, such as at a location distal to the thoracic cardiac branch 128 or at a nerve branch.
2. Using Function 2 described above (i.e., transmitting data) of external electronic appliance 200 and external appliance 190, implantable stimulator 150 is commanded to produce a series of electrical stimulation pulses with gradually increasing amplitude.
3. After each stimulation pulse, series of pulses, or at some other predefined interval, any change in, e.g., EEG and/or neurotransmitter and/or medication level is sensed, for instance, by one or more electrodes 156 and 158 or sensors (e.g., a CHEMFET). These responses are converted to data and telemetered out to external electronic appliance 200 via Function 3.
4. From the response data received at external appliance 200 from the implantable stimulator 150, or from other assessment, the stimulus threshold for obtaining a response is determined and is used by a clinician acting directly 212 or by other computing means 218 to transmit the desired stimulation parameters to the implantable stimulator 150 in accordance with Function 2.
5. When patient 170 desires to invoke electrical stimulation to alleviate symptoms, patient 170 employs controller 180 to set the implantable stimulator 150 in a state where it delivers a prescribed stimulation pattern from a predetermined range of allowable stimulation patterns.
6. To cease electrical stimulation, patient 170 employs controller 180 to turn off stimulator 150.
7. Periodically, the patient or caregiver recharges the power source/storage device 162 of implantable stimulator 150, if necessary, in accordance with Function 1 described above (i.e., transmit electrical power).

For the treatment of any of the various types and degrees of medical conditions as mentioned herein, it may be desirable to modify or adjust the algorithmic functions performed by the implanted and/or external components, as well as the surgical approaches, in ways that would be obvious to skilled practitioners of these arts. For example, in some situations, it may be desirable to employ more than one implantable stimulator 150, each of which could be separately controlled by means of a digital address. Multiple channels and/or multiple patterns of stimulation might thereby be programmed by the clinician and controlled by the patient in order to, for instance, stimulate larger areas of neural tissue in order to maximize therapeutic efficacy.

In some embodiments discussed earlier, microstimulator 150, or a group of two or more microstimulators, is controlled via closed-loop operation. A need for and/or response to stimulation is sensed via microstimulator 150, or by an additional microstimulator (which may or may not be dedicated to the sensing function), or by another implanted or external device. If necessary, the sensed information is transmitted to microstimulator 150. In some embodiments, the stimulation parameters used by microstimulator 150 are automatically adjusted based on the sensed information. Thus, the stimulation parameters are adjusted in a closed-loop manner to provide stimulation tailored to the need for and/or response to stimulation.

For instance, in some embodiments of the present disclosure, a first and second "stimulator" are provided. The second "stimulator" periodically (e.g. once per minute) records e.g., limb tremor (via accelerometer or muscle EMG), which it transmits to the first stimulator. The first stimulator uses the sensed information to adjust stimulation parameters according to an algorithm programmed, e.g., by a clinician. For example, stimulation amplitude may be increased in response to increased acceleration or increased EMG amplitude or activity. Alternatively, one "microstimulator" performs both the sensing and stimulating functions.

Figure 5:
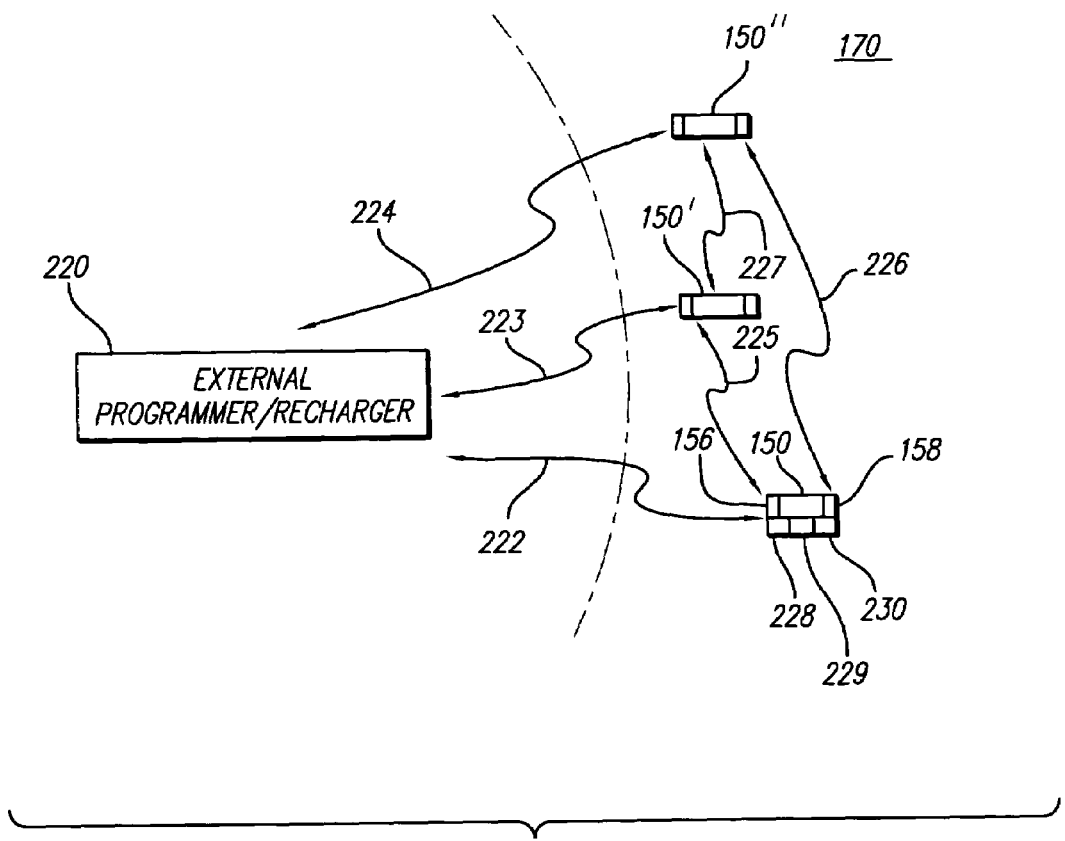
FIG. 5 depicts a system of implantable devices that communicate with each other and/or with external control/programming devices.

For example, as shown in the example of FIG. 5, a first microstimulator 150, implanted beneath the skin of patient 170, provides electrical stimulation via electrodes 156 and 158 to a first location; a second microstimulator 150' provides electrical stimulation to a second location; and a third microstimulator 150" provides electrical stimulation to a third location. As mentioned earlier, the implanted devices may operate independently or may operate in a coordinated manner with other similar implanted devices, other implanted devices, or other devices external to the patient's body, as shown by the control lines 222, 223 and 224 in FIG. 5. That is, in accordance with certain embodiments of the present disclosure, external controller 220 controls the operation of each of the implanted microstimulators 150, 150' and 150". According to various embodiments of the present disclosure, an implanted device, e.g. microstimulator 150, may control or operate under the control of another implanted device(s), e.g., microstimulator 150' and/or microstimulator 150". That is, a device made in accordance with the present disclosure may communicate with other implanted stimulators, other implanted devices, and/or devices external to a patient's body, e.g., via an RF link, an ultrasonic link, a thermal link, an optical link, or other communications link. Specifically, as illustrated in FIG. 5, microstimulator 150, 150', and/or 150", made in accordance with the present disclosure, may communicate with an external remote control (e.g., patient and/or physician programmer 220) that is capable of sending commands and/or data to implanted devices and that may also be capable of receiving commands and/or data from implanted devices.

A microstimulator made in accordance with the present disclosure may incorporate, in some embodiments, first sensing means 228 for sensing therapeutic effects, clinical variables, or other indicators of the state of the patient, such as EEG, ENG, EMG, abnormal movements, limb tremor, and/or head tremor. The stimulator additionally or alternatively incorporates second means 229 for sensing levels or changes in one or more medications, neurotransmitters, hormones, cytokines, enzymes, and/or other substances in the blood plasma, in the cerebrospinal fluid, or in the local interstitial fluid. The stimulator additionally or alternatively incorporates third means 230 for sensing electrical current levels and/or waveforms supplied by another source of electrical energy. Sensed information may be used to control the parameters of the stimulator(s) in a closed loop manner, as shown by control lines 225, 226, and 227. Thus, the sensing means may be incorporated into a device that also includes electrical stimulation means, or the sensing means (that may or may not have stimulating means) may communicate the sensed information to another device(s) with stimulating means.

While a microstimulator may also incorporate means of sensing the condition of a patient, e.g., via EEG, ENG, or EMG, it may alternatively or additionally be desirable to use a separate or specialized implantable device to sense and telemeter physiological conditions/responses in order to adjust stimulation parameters. This information may be transmitted to an external device, such as external appliance 220, or may be transmitted directly to implanted stimulator(s) 150. However, in some cases, it may not be necessary or desired to include a sensing function or device, in which case stimulation parameters may be determined and refined, for instance, by patient feedback.

Again, microstimulator(s) 150 may be implanted adjacent to the vagus nerve 100, for instance, distal to the superior cervical cardiac branch 120, or distal to both the superior cervical cardiac branch 120 and the inferior cervical cardiac branch 124, and may be adjacent to the left vagus nerve. Alternatively or additionally, one or more simulators may be implanted adjacent to the vagus nerve 100 distal to the thoracic cardiac branch 128, for instance, also on the left.

As described above, stimulation of the vagus nerve may include stimulation at a vagus nerve branch(es). For instance, the pharyngeal branch of the vagus nerve 130, the superior laryngeal branch of the vagus nerve 132, the pharyngeal plexus (not shown), the left and/or right recurrent laryngeal branch of the vagus nerve 134, and/or other pharyngeal and/or laryngeal branches of the vagus nerve may be stimulated to relieve sleep disorders. As another example, one or more of the gastrointestinal branches of the vagus nerve, such as the anterior gastric branch of the anterior vagal trunk 138, the right gastric plexus 140, and/or the left gastric plexus 142 may be stimulated to relieve gastrointestinal disorders. As yet another example, one or more branches innervating the pancreas, such as the anterior superior and anterior inferior pancreaticoduodenal plexus 146, the posterior pancreaticoduodenal plexus (not shown), the inferior pancreaticoduodenal plexus 148, or the like may be stimulated to relieve endocrine disorders.

According to several embodiments of the present disclosure, symptoms of certain types of epilepsy, mood disorders (e.g., depression), metabolic disorders (e.g., certain types of obesity), cardiac disorders (e.g., tachycardia) and/or gastrointestinal disorders (e.g., gastroparesis), are alleviated by increasing excitement of certain of these nerve fibers. Relatively low-frequency electrical stimulation (e.g., less than about 50–100 Hz) is likely to produce such excitement.

According to various embodiments of the present disclosure, symptoms of certain other types of cardiac disorders (e.g. bradycardia, where parasympathetic activity to the heart is disrupted and heart rate increases) and/or metabolic disorders (e.g., to decrease digestive activity in certain types of obesity), are alleviated by alternatively decreasing excitement of certain of these nerve fibers. Relatively high-frequency electrical stimulation (e.g., greater than about 50–100 Hz) is likely to produce such inhibition.

Additionally, sensing means described earlier may be used to orchestrate first the activation of microstimulator(s) targeting one area of the vagus nerve, and then, when appropriate, the microstimulator(s) targeting the same or another area of the nerve, in order to control symptoms, for instance, by a different means. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims.

What is claimed is:

1. A method for treating a patient with an endocrine disorder, comprising:
   generating stimulation pulses with an implanted stimulator in accordance with one or more stimulation parameters, the stimulator being coupled to at least two implanted electrodes; and
   delivering the stimulation pulses via the at least two electrodes to at least one or more of an anterior superior pancreaticoduodenal plexus, an anterior inferior pancreaticoduodenal plexus, a posterior pancreaticoduodenal plexus, and an inferior pancreaticoduodenal plexus;
   wherein the stimulation pulses are configured to treat the endocrine disorder.

2. The method of claim 1, further comprising:
   providing a sensor;
   using the sensor to sense a physical condition; and
   using the sensed condition to determine the stimulation parameters.

3. The method of claim 2 wherein the sensor senses at least one of electrical activity of the brain, electrical activity of a nerve, muscle activity, limb tremor, head tremor, and patient movement.

4. The method of claim 2 wherein the sensor senses at least one of medication level, neurotransmitter level, hormone level, cytokine level, enzyme level, level of a blood-borne substance, and level of a substance in the cerebrospinal fluid.

5. The method of claim 2, wherein the sensor comprises at least one or more of a chemically sensitive field-effect transistor.

6. The method of claim 2, wherein one or more of the electrodes are configured to serve as the sensor.

7. The method of claim 2, further comprising communicating data representing the sensed physical condition to the stimulator.

8. The method of claim 2, further comprising determining the stimulation parameters based on the sensed condition in a closed loop manner.

9. The method of claim 1 wherein the stimulation parameters are determined using at least one external appliance.

10. The method of claim 1, further comprising providing power to the stimulator with at least one external appliance.

11. The method of claim 10 wherein providing power to the at least one stimulator further comprises storing the power received from the at least one external appliance.

12. The method of claim 1 further comprising providing and implanting more than one stimulator.

13. The method of claim 1 wherein the stimulation pulses are delivered at less than 100 Hz.

14. The method of claim 1 wherein the stimulation pulses are configured to relieve symptoms of the endocrine disorder.

15. The method of claim 1 wherein the stimulation pulses are delivered at a frequency that is greater than 100 Hz.

16. The method of claim 1, wherein the at least two electrodes are disposed on a surface of the stimulator.

17. The method of claim 1, wherein the stimulator comprises multiple stimulators.

18. The method of claim 17, wherein the multiple stimulators comprise at least a first stimulator and a second stimulator, and wherein the method further comprises:
    sensing a physical condition related to the endocrine disorder with the first stimulator; and
    generating with the second stimulator the stimulation pulses in accordance with the sensed physical condition.

19. The method of claim 1, further comprising implanting the stimulator no more than about 150 millimeters from at least one or more of the anterior superior pancreaticoduodenal plexus, the anterior inferior pancreaticoduodenal plexus, the posterior pancreaticoduodenal plexus, and the inferior pancreaticoduodenal plexus.

* * * * *